(12) United States Patent
Dawis et al.

(10) Patent No.: US 7,722,681 B2
(45) Date of Patent: May 25, 2010

(54) COMPOSITIONS FOR TREATING HAIR AND METHODS OF USE

(75) Inventors: Suzanne Dawis, Florence, KY (US); Vincent Fischer, St. Petersburg, FL (US)

(73) Assignee: Kao Brands Company, Cincinnati, OH (US)

( * ) Notice: Subject to any disclaimer, the term of this patent is extended or adjusted under 35 U.S.C. 154(b) by 136 days.

(21) Appl. No.: 11/871,500

(22) Filed: Oct. 12, 2007

(65) Prior Publication Data

US 2009/0094762 A1    Apr. 16, 2009

(51) Int. Cl.
*A61Q 5/10*    (2006.01)
(52) U.S. Cl. .............. 8/405; 8/431; 8/435; 8/455; 8/463; 8/494; 8/632
(58) Field of Classification Search ............ 8/405, 8/431, 435, 455, 463, 594, 632
See application file for complete search history.

(56) References Cited

U.S. PATENT DOCUMENTS

| | | | |
|---|---|---|---|
| 5,643,341 A | 7/1997 | Hirsch et al. | |
| 5,690,921 A | 11/1997 | Lang et al. | |
| 5,843,193 A | 12/1998 | Hawkins et al. | |
| 6,908,491 B2 | 6/2005 | Fischer et al. | |
| 2005/0226838 A1* | 10/2005 | Krause et al. | 424/70.13 |
| 2005/0260146 A1 | 11/2005 | Blin | |
| 2007/0006399 A1* | 1/2007 | Carrascal et al. | 8/409 |

FOREIGN PATENT DOCUMENTS

| EP | 0 970 685 A1 | 1/2000 |
|---|---|---|
| WO | WO 02/102350 A2 | 12/2002 |
| WO | WO 2004/103335 A1 | 12/2004 |

OTHER PUBLICATIONS

Gomes et al., "The Use of Silicones in Hair Colorant Formulations", Dow Corning (2000).

* cited by examiner

*Primary Examiner*—Eisa B Elhilo
(74) *Attorney, Agent, or Firm*—Morris, Manning & Martin, LLP; Christopher W. Raimund

(57) ABSTRACT

Compositions comprising one or more acid direct dyes and an organic solvent such as propylene carbonate are described. The compositions have an oil phase content of 5 percent by weight or less. The oil phase of the compositions can include a cyclopentasiloxane and dimethiconol. The compositions can be applied to hair that has been previously dyed with an oxidative hair dye composition to restore color to the hair. The compositions can also be applied to hair that has not been previously treated with an oxidative hair dye composition. Methods of applying these compositions to hair are also described. The methods involve applying the composition to wet hair, allowing the composition to remain on the hair, and subsequently rinsing the composition from the hair with water. The hair may be treated with a conditioner before applying the compositions to the hair.

16 Claims, No Drawings

COMPOSITIONS FOR TREATING HAIR AND METHODS OF USE

BACKGROUND

1. Technical Field

This application relates generally to compositions for treating keratin and methods of use, and, in particular, to compositions comprising one or more acid direct dyes and to methods of applying these compositions to hair to impart color thereto.

2. Background of the Technology

It is well appreciated that individuals often wish to cosmetically alter the coloring of their hair by various known hair coloring treatments and that many individuals change their own hair color to their favorite hair color using currently available hair dye compositions. In particular, oxidative dye compositions are commonly used because such compositions simultaneously decolorize and dye hair, thus widening the degree of freedom of hair color. Thus, individuals having comparatively dark hair are able to use such products. Moreover, the products provide a greater number of color variations.

Use of oxidative dye compositions to treat hair is typically expensive and can be time consuming as well. In addition, the chemicals employed in these treatments can be caustic and somewhat damaging to the hair. Their frequent use is not preferred, and rather they are generally used at intervals of at least about one month. It is unavoidable that the color of hair dyed with oxidative dye compositions gradually fades during this one month owing to the influence of washing with shampoo, sweat, ultraviolet rays from sunshine and the like. The gradual fading of color results in a gradual reduction in the feeling of satisfaction generally felt immediately after dyeing.

Thus, individuals who have had their hair color-treated are often desirous of prolonging the effects of treatment for as long as possible and otherwise wish to keep their hair in as healthy a state as possible between visits to the colorist. One way of prolonging the freshness of a hair coloring treatment and to otherwise preserve the condition of the hair is to use hair color maintenance shampoos, conditioners, rinses, mousses, gels, sprays and the like. Examples of such hair color maintenance products include AVEDA™ shampoos and conditioners; TRICOL™ Color Plus™ products; ARTec Color Enhancing shampoos and conditioners; LOGICS™ Color Refresher™; and UTENA™ Cha Charl™. Such hair color maintenance products are typically formulated with a degree of coloring, so as to assist an individual in an attempt to prolong the duration of the coloring treatment. These products have a number of drawbacks, however. For example, such products require daily use in order to maintain hair color. Furthermore, such products are low in hair dyeing power, thus being insufficient for revitalizing fading color.

Methods for maintaining hair color are also disclosed in U.S. Pat. No. 5,643,341. In addition, a color refreshing rinse has been sold under the name ROUX® Fanciful®.

There still exists a need for improved color revitalizing products for hair that has been previously treated with an oxidative dye composition to supply color to the hair that has been lost by washing or shampooing. In addition, since untreated hair also fades when exposed to sunlight, shampooing and styling tools such as curling irons and dryers, there also exists a need for improved products which can be used on hair that has not been previously treated with an oxidative dye composition to impart color thereto.

SUMMARY

According to a first embodiment, a composition is provided which comprises:
one or more acid direct dyes;
an organic solvent; and
an oil phase;
wherein the oil phase content of the composition is 5 percent by weight or less and wherein the composition has a pH of 2-6.

According to a second embodiment, a method is provided which comprises:
applying a composition as set forth above to hair;
allowing the composition to remain on the hair; and
subsequently rinsing the composition from the hair with water.

DETAILED DESCRIPTION

A system and method for color-revitalizing hair is disclosed in U.S. Pat. No. 6,908,491 B2, which is incorporated by reference herein in its entirety. The compositions disclosed in this patent include at least one direct dye (e.g., an acid direct dye). The compositions disclosed in this patent also include, in addition to the direct dyes, propylene carbonate, ethanol, xanthan gum, a polyether modified silicone, lactic acid, sodium hydroxide, a perfume base and water. These compositions can be applied to hair previously dyed with an oxidative hair dye composition.

Various formulations designed to restore color to hair are currently being sold under the "John Frieda Luminous Color Glaze". These formulations have a base formula as set forth in the following table:

| Material Description | % Weight/% Weight |
|---|---|
| Propylene Carbonate | 15.0000 |
| Xanthan Gum | 1.5000 |
| Ethanol | 4.9500-5.0000 |
| Sodium Hydroxide | 0.1000 |
| Citric Acid | 2.5550 |
| Methylchloroisothiazolinone (and) Methylisothiazolinone | 0.0700 |
| PEG-12 Dimethicone | 2.4000 |
| Hydrogenated Polydecene | 2.0000 |
| Oleyl Alcohol | 1.0000 |
| Dimethicone | 2.6400 |
| Dimethiconol | 0.3600 |
| Deionized Water | QS to 100% |
| Frangrance, Extracts and Pigments | Less than 2% |

These products also include various combinations of acid dyes. For example, the "Luminous Glaze" products for blonde and brunette hair include combinations of Orange 4, Yellow 10, and External Violet 2 whereas the products for red hair include either a combination of Orange 4, Red 33, and External Violet 2 or a combination of Orange 4 and Red 33. These products are oil-in-water dispersions having an oil phase content of about 8.4 percent by weight based on the total weight of the composition. The oil phase of these composition includes Hydrogenated Polydecene, Oleyl Alcohol, PEG-12 Dimethicone, Dimethicone and Dimethiconol.

The compositions described herein have an oil phase content of 5 percent by weight or less based on the total weight of the composition. These compositions can be applied to either undyed hair or to previously dyed hair (e.g., to hair previously treated with an oxidative dye composition). These compositions include an organic solvent and an acid direct dye. Examples of the acid direct dye include Yellow No. 203 (D & C Yellow No. 10, Color Index (CI) given as (CI 47005)), Orange No. 205 (D & C Orange No. 4 (CI 15510)), Red No. 227 (D & C Red No. 33 (CI (Color index) 17200)), Violet No. 401 (Ext. D & C Violet No. 2 (CI 607301)) and Black No. 401 (CI 20470). The compositions can include an acid direct dye or a combination of acid direct dyes selected from the group consisting of Yellow No. 10, Orange No. 4, External Violet No. 2, Red No. 33 and combinations thereof. For example, compositions for blonde and brunette hair can include combinations of Orange 4, Yellow 10 and External Violet 2 and compositions for red hair can include either a combination of Orange 4, Red 33, and External Violet 2 or a combination of Orange 4 and Red 3.

According to a one embodiment, the composition comprises one or more acid direct dyes, an organic solvent and a cyclic dimethyl polysiloxane compound. According to a further embodiment, the composition comprises one or more acid direct dyes, one or more carboxylic acid compounds, and an organic solvent, wherein the one or more carboxylic acid compounds includes malic acid.

Examples of the organic solvent include benzyl alcohol, 2-benzyloxyethanol, propylene carbonate, gamma-butyrolactone and N-methylpyrrolidone. An exemplary solvent is propylene carbonate which has an empirical formula of $C_4H_6O_3$ and a chemical structure as set forth below:

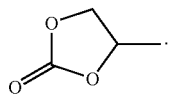

The compositions can also comprise one or more preservatives. Exemplary preservatives include methylchloroisothiazolinone, methylisothiazolinone and combinations thereof.

A thickener may also be added to the composition to prevent running and the like, thereby facilitating its application to hair. An exemplary thickener is xanthan gum.

The compositions may also include a solubilizing agent for the organic solvent in water. Ethanol, propylene glycol or the like can be used as the solubilizing agent.

The compositions have an acidic pH. For example, the compositions can have a pH of 2 to 6, particularly a pH of 2 to 5, and more particularly a pH of 2 to 4. The adjustment of the pH may be conducted in accordance with any known method.

The compositions may also include an inorganic base such as sodium hydroxide as well as an organic carboxylic acid. Exemplary organic carboxylic acids include citric acid, malic acid and combinations thereof.

The composition can further comprise a component selected from the group consisting of: *Theobromo Cacao* Extract; *Camellia Sinensis* Leaf Extract; *Fragaria Vesca* (Strawberry) Fruit Extract; *Zingiber Officinale* Leaf Extract; *Prunus Domestica* Fruit; *Punic Granatum* Leaf Extract; *Helianthus Annuus* (Sunflower) Seed Extract; *Citrus Medica Limonum* (Lemon) Peel Extract; *Chamomilla Recutita* (Matricaria) Flower Extract; *Helianthus Annuus* (Sunflower) Seed Oil; *Triticum Vulgare* (Wheat) Germ Oil; and *Triticum Vulgare* (Wheat) Germ Extract. Compositions formulated for brown hair can include *Theobromo Cacao* Extract, *Camellia Sinensis* Leaf Extract or combinations thereof. Compositions formulated for red hair can include *Fragaria Vesca* (Strawberry) Fruit Extract (and) *Zingiber Officinale* Leaf Extract, *Prunus Domestica* Fruit (and) *Punic Granatum* Leaf Extract or combinations thereof. Compositions formulated for blonde hair can include *Helianthus Annuus* (Sunflower) Seed Extract; *Citrus Medica Limonum* (Lemon) Peel Extract; *Chamomilla Recutita* (Matricaria) Flower Extract, *Helianthus Annuus* (Sunflower) Seed Oil, *Triticum Vulgare* (Wheat) Germ Extract, *Triticum Vulgare* (Wheat) Germ Oil and combinations thereof.

Compositions formulated for brown hair can also include pearl powder. Compositions formulated for blonde hair can also include panthenol, tocopheryl acetate and/or hydroxypropyltrimonium honey. Compositions formulated for red hair can also include tocopheryl acetate, magnesium ascorbyl palmitate and retinyl palmitate.

The compositions can also include mica, iron oxides, titanium oxide and combinations thereof. For example, compositions formulated for blonde hair can include mica and titanium dioxide. Compositions formulated for red hair can include iron oxide and mica and, optionally, titanium dioxide. Compositions formulated for brown hair can include iron oxide and mica and titanium dioxide.

The compositions can also include a fragrance.

According to one embodiment, the composition is in the form of an oil-in-water emulsion having an oil phase content of 5% by weight or less based on the total weight of the composition. According to a further embodiment, the composition is in the form of an oil-in-water dispersion having an oil phase content of 3% by weight or less or from 2.0 to 3.0 percent by weight based on the total weight of the composition.

According to a further embodiment, a composition is provided which comprises, as an oil phase, 2.5 percent by weight based on the total weight of the composition of a silicone fluid. The silicone fluid can be a combination of cyclopentasiloxane (and) dimethiconol. Compositions comprising 2.5 percent by weight based on the total weight of the composition of a combination of cyclopentasiloxane and dimethiconol were evaluated and were surprisingly found to impart satisfactory levels of hair conditioning without producing a greasy feel.

When a composition comprising an acid direct dye and/or an organic solvent and having an acidic pH is used as the color-revitalizing composition, the dullness of hair is improved, and a feeling of transparency, luster, shine, structure, body, deep shade and manageability is imparted to the hair.

The color-revitalizing compositions used in the present invention may be prepared in the form of a gel, a cream, a liquid, a foam or the like and may also be provided in the form of an aerosol.

Methods for applying the compositions include a method in which either dry hair or wetted hair is coated with an amount of the composition sufficient to evenly spread the composition throughout the hair. The composition is then left to stand for a period of time (e.g., 3 to 45 minutes), rinsed out with warm water, optionally shampooed and rinsed, and then dried. An alternative method is one in which hair that has been shampooed and wiped with a towel is coated with an amount of the composition sufficient to evenly spread the composition throughout the hair, left to stand for 3 to 45 minutes, rinsed out with warm water, optionally shampooed and rinsed, and then dried. The hair may also be conditioned after shampooing and before or after treatment with the composition.

The composition and method of the invention is simple and does not require large amounts of time to carry out. An example of a method of applying the composition to hair includes:

uniformly apply the composition to damp hair;
leave in for 3 minutes;
rinse out; and
proceed with normal hair care routine.

The composition can be applied to the hair using gloves to prevent staining of the user's skin. The compositions can be applied weekly or more or less frequently as necessary to maintain beautiful hair color.

If desired, one can preview the results prior to use by doing a simple strand test as follows:

1) dampen an underneath section of hair (½ to 1 inch);
2) apply the color revitalization composition (about a dime size) and massage in thoroughly;
3) after approximately 3 to 10 minutes, then rinse;
4) dry and inspect hair to confirm the color restoration.

Another example of a protocol for applying the color revitalizing composition of the invention includes:

dampen hair (i.e., such that the hair is not soaking wet);
using gloves, squeeze about a half-dollar sized amount into palm of hand (about 2 tablespoons);
adjust the amount used as necessary for length of type of hair;
massage into hair;
rub in until all hair is uniformly covered;
leave in hair for 10 minutes;
shampoo the composition out of the hair; and
rinse until the rinse water is free from coloration.

The user can then proceed with a normal hair care and styling routine.

The compositions can be applied about one to three times a week to maintain a beautiful, shiny, fresh-colored look. More frequent use will increase the coloring effect, if desired.

Specific formulations are set forth in the following table. Formulations I-VI include various combinations of acid dyes which can be applied to hair to achieve a desired coloring effect. In particular, formulation I imparts a "chestnut" color to the hair of a user, formulation II imparts a "amber" color to the hair of a user, formulations III and IV impart a red color to the hair of a user, formulation V imparts a "platinum" color to the hair of a user, and formulation VI imparts a "honey" color to the hair of a user.

| | Shade | | | | | |
|---|---|---|---|---|---|---|
| | I | II | III | IV | V | VI |
| | Chestnut | Amber | Vivid Red | Richer Red | Platinum | Honey |
| Material Description | % Wt./Wt. | % Wt./Wt. | % Wt./Wt. | % Wt./Wt. | % Wt./Wt. | % Wt./Wt. |
| WATER | 72.7621550 | 72.7855650 | 72.6023600 | 72.5944600 | 72.8365244 | 72.8314244 |
| PROPYLENE CARBONATE | 15.0000000 | 15.0000000 | 15.0000000 | 15.0000000 | 15.0000000 | 15.0000000 |
| ALCOHOL DENAT. | 4.9500000 | 4.9500000 | 4.9500000 | 4.9500000 | 4.9500000 | 4.9500000 |
| CITRIC ACID | 2.5550000 | 2.5550000 | 2.5550000 | 2.5550000 | 2.5550000 | 2.5550000 |
| CYCLOPENTASILOXANE | 2.1250000 | 2.1250000 | 2.1250000 | 2.1250000 | 2.1250000 | 2.1250000 |
| XANTHAN GUM NF | 1.5000000 | 1.5000000 | 1.5000000 | 1.5000000 | 1.5000000 | 1.5000000 |
| DIMETHICONOL | 0.3750000 | 0.3750000 | 0.3750000 | 0.3750000 | 0.3750000 | 0.3750000 |
| SODIUM HYDROXIDE | 0.1000000 | 0.1000000 | 0.1000000 | 0.1000000 | 0.1000000 | 0.1000000 |
| PROPYLENE GLYCOL | 0.0004850 | 0.0004850 | 0.0048500 | 0.0048500 | 0.0001056 | 0.0001056 |
| METHYLCHLOROISOTHIAZOLINONE | 0.0008050 | 0.0008050 | 0.0008050 | 0.0008050 | 0.0008050 | 0.0008050 |
| METHYLISOTHIAZOLINONE | 0.0002450 | 0.0002450 | 0.0002450 | 0.0002450 | 0.0002450 | 0.0002450 |
| MALIC ACID | 0.0050000 | 0.0050000 | 0.0050000 | 0.0050000 | 0.0050000 | 0.0050000 |
| PANTHENOL | | | | | 0.0005000 | 0.0005000 |
| *HELIANTHUS ANNUUS* (SUNFLOWER) SEED OIL | | | | | 0.0010000 | |
| TOCOPHERYL ACETATE USP/FCC | | | | | | 0.0010000 |
| HYDROXYPROPYLTRIMONIUM HONEY | | | | | | 0.0010000 |
| *TRITICUM VULGARE* (WHEAT) GERM OIL | | | | | | 0.0010000 |
| PEARL POWDER | 0.0010000 | 0.0010000 | | | | |
| *HELIANTHUS ANNUUS* (SUNFLOWER) SEED EXTRACT | | | | | 0.0000034 | |
| *CITRUS MEDICA LIMONUM* (LEMON) PEEL EXTRACT | | | | | 0.0000033 | |
| *CHAMOMILLA RECUTITA* (MATRICARIA) FLOWER EXTRACT | | | | | 0.0000033 | |
| HONEY EXTRACT | | | | | | 0.0000050 |
| *TRITICUM VULGARE* (WHEAT) GERM EXTRACT | | | | | | 0.0000050 |
| *CAMELLIA SINENSIS* LEAF EXTRACT | | 0.0001000 | | | | |
| *THEOBROMA CACAO* (COCOA) EXTRACT | 0.0000100 | | | | | |
| ALCOHOL | | | 0.0003300 | 0.0003300 | | |
| LECITHIN | | | 0.0010000 | 0.0010000 | | |
| TOCOPHERYL ACETATE | | | 0.0002600 | 0.0002600 | | |
| MAGNESIUM ASCORBYL PHOSPHATE | | | 0.0002000 | 0.0002000 | | |
| RETINYL PALMITATE | | | 0.0000500 | 0.0000500 | | |
| *FRAGARIA VESCA* (STRAWBERRY) FRUIT EXTRACT | | | 0.0000500 | 0.0000500 | | |
| *ZINGIBER OFFICINALE* (GINGER) ROOT EXTRACT | | | 0.0000500 | 0.0000500 | | |
| FRAGRANCE | 0.4000000 | 0.4000000 | 0.6000000 | 0.6000000 | 0.4000000 | 0.4000000 |
| MICA | 0.0840000 | 0.0840000 | 0.0735000 | 0.0735000 | 0.1050000 | 0.1050000 |
| TITANIUM DIOXIDE | 0.0060000 | 0.0060000 | | | 0.0450000 | 0.0450000 |
| IRON OXIDES | 0.0600000 | 0.0600000 | 0.0765000 | 0.0765000 | | |
| EXT. VIOLET 2 | 0.0319000 | 0.0217000 | | 0.0086000 | 0.0001100 | 0.0006600 |
| YELLOW 10 | 0.0098000 | 0.0067000 | | | 0.0002300 | 0.0010700 |

-continued

| | Shade | | | | | |
|---|---|---|---|---|---|---|
| Material Description | I Chestnut % Wt./Wt. | II Amber % Wt./Wt. | III Vivid Red % Wt./Wt. | IV Richer Red % Wt./Wt. | V Platinum % Wt./Wt. | VI Honey % Wt./Wt. |
| ORANGE 4 | 0.0336000 | 0.0234000 | 0.0214000 | 0.0233000 | 0.0004700 | 0.0021800 |
| RED 33 | | | 0.0084000 | 0.0058000 | | |

Additional formulations are set forth in the following table.

| | INCI | | | | | |
|---|---|---|---|---|---|---|
| Material Description | Platinum % wt./wt. | Honey % wt./wt. | Amber % wt./wt. | Chestnut % wt./wt. | Brighter Vivid Red % wt./wt. | Richer Red % wt./wt. |
| WATER | 66.9365244 | 66.9314244 | 66.8855650 | 66.8621550 | 66.7023600 | 66.6944600 |
| PROPYLENE CARBONATE | 15.0000000 | 15.0000000 | 15.0000000 | 15.0000000 | 15.0000000 | 15.0000000 |
| ALCOHOL DENAT. | 4.9500000 | 4.9500000 | 4.9500000 | 4.9500000 | 4.9500000 | 4.9500000 |
| CITRIC ACID | 2.5550000 | 2.5550000 | 2.5550000 | 2.5550000 | 2.5550000 | 2.5550000 |
| PEG-12 DIMETHICONE | 2.4000000 | 2.4000000 | 2.4000000 | 2.4000000 | 2.4000000 | 2.4000000 |
| DIMETHICONE | 2.6400000 | 2.6400000 | 2.6400000 | 2.6400000 | 2.6400000 | 2.6400000 |
| HYDROGENATED POLYDECENE | 2.0000000 | 2.0000000 | 2.0000000 | 2.0000000 | 2.0000000 | 2.0000000 |
| XANTHAN GUM NF | 1.5000000 | 1.5000000 | 1.5000000 | 1.5000000 | 1.5000000 | 1.5000000 |
| OLEYL ALCOHOL | 1.0000000 | 1.0000000 | 1.0000000 | 1.0000000 | 1.0000000 | 1.0000000 |
| DIMETHICONOL | 0.3600000 | 0.3600000 | 0.3600000 | 0.3600000 | 0.3600000 | 0.3600000 |
| SODIUM HYDROXIDE | 0.1000000 | 0.1000000 | 0.1000000 | 0.1000000 | 0.1000000 | 0.1000000 |
| PROPYLENE GLYCOL | 0.0001056 | 0.0001056 | 0.0004850 | 0.0004850 | 0.0048500 | 0.0048500 |
| METHYLCHLOROISOTHIAZOLINONE | 0.0008050 | 0.0008050 | 0.0008050 | 0.0008050 | 0.0008050 | 0.0008050 |
| METHYLISOTHIAZOLINONE | 0.0002450 | 0.0002450 | 0.0002450 | 0.0002450 | 0.0002450 | 0.0002450 |
| MALIC ACID | 0.0050000 | 0.0050000 | 0.0050000 | 0.0050000 | 0.0050000 | 0.0050000 |
| PANTHENOL | 0.0005000 | 0.0005000 | | | | |
| *HELIANTHUS ANNUUS* (SUNFLOWER) SEED OIL | 0.0010000 | | | | | |
| TOCOPHERYL ACETATE USP/FCC | | 0.0010000 | | | | |
| HYDROXYPROPYLTRIMONIUM HONEY | | 0.0010000 | | | | |
| *TRITICUM VULGARE* (WHEAT) GERM OIL | | 0.0010000 | | | | |
| PEARL POWDER | | | 0.0010000 | 0.0010000 | | |
| *HELIANTHUS ANNUUS* (SUNFLOWER) SEED EXTRACT | 0.0000034 | | | | | |
| *CITRUS MEDICA LIMONUM* (LEMON) PEEL EXTRACT | 0.0000033 | | | | | |
| *CHAMOMILLA RECUTITA* (MATRICARIA) FLOWER EXTRACT | 0.0000033 | | | | | |
| HONEY EXTRACT | | 0.0000050 | | | | |
| *TRITICUM VULGARE* (WHEAT) GERM EXTRACT | | 0.0000050 | | | | |
| *CAMELLIA SINENSIS* LEAF EXTRACT | | | 0.0001000 | | | |
| *THEOBROMA CACAO* (COCOA) EXTRACT | | | | 0.0000100 | | |
| ALCOHOL | | | | | 0.0003300 | 0.0003300 |
| LECITHIN | | | | | 0.0010000 | 0.0010000 |
| TOCOPHERYL ACETATE | | | | | 0.0002600 | 0.0002600 |
| MAGNESIUM ASCORBYL PHOSPHATE | | | | | 0.0002000 | 0.0002000 |
| RETINYL PALMITATE | | | | | 0.0000500 | 0.0000500 |
| *FRAGARIA VESCA* (STRAWBERRY) FRUIT EXTRACT | | | | | 0.0000500 | 0.0000500 |
| *ZINGIBER OFFICINALE* (GINGER) ROOT EXTRACT | | | | | 0.0000500 | 0.0000500 |
| FRAGRANCE | 0.4000000 | 0.4000000 | 0.4000000 | 0.4000000 | 0.6000000 | 0.6000000 |
| MICA | 0.1050000 | 0.1050000 | 0.0840000 | 0.0840000 | 0.0735000 | 0.0735000 |
| TITANIUM DIOXIDE | 0.0450000 | 0.0450000 | 0.0060000 | 0.0060000 | | |
| IRON OXIDES | | | 0.0600000 | 0.0600000 | 0.0765000 | 0.0765000 |
| EXT. VIOLET 2 | 0.0001100 | 0.0006600 | 0.0217000 | 0.0319000 | | 0.0086000 |
| YELLOW 10 | 0.0002300 | 0.0010700 | 0.0067000 | 0.0098000 | | |
| ORANGE 4 | 0.0004700 | 0.0021800 | 0.0234000 | 0.0336000 | 0.0214000 | 0.0233000 |
| RED 33 | | | | | 0.0084000 | 0.0058000 |

Generalized formulation ranges are set forth in the following table.

| FUNCTION | May include: INCI | FUNCTIONAL RANGE |
|---|---|---|
| Organic Solvent | PROPYLENE CARBONATE<br>ALCOHOL DENAT.<br>ALCOHOL | 1-50% |
| Oil Phase | CYCLOPENTASILOXANE<br>DIMETHICONOL<br>PEG-12 DIMETHICONE<br>DIMETHICONE<br>HYDROGENATED POLYDECENE<br>OLEYL ALCOHOL<br>TOCOPHERYL ACETATE USP/FCC<br>*TRITICUM VULGARE* (WHEAT) GERM OIL<br>*HELIANTHUS ANNUUS* (SUNFLOWER) SEED OIL<br>TOCOPHERYL ACETATE USP/FCC<br>RETINYL PALMITATE<br>FRAGRANCE | 1-30% |
| Hair dye composition | EXT. VIOLET 2<br>YELLOW 10<br>ORANGE 4<br>RED 33 | The acid dyes may be used either singly or in any combination thereof. They may be incorporated in a proportion of 0.001-5% by weight (hereinafter indicated merely by "%"), particularly 0.005-4%, more particularly 0.2-3% based on the total weight of the composition |
| Buffer/Acid system | CITRIC ACID<br>SODIUM HYDROXIDE<br>MALIC ACID | pH of 2-6 |
| Excipient | WATER<br>XANTHAN GUM NF<br>PROPYLENE GLYCOL<br>METHYLCHLOROISOTHIAZOLINONE<br>METHYLISOTHIAZOLINONE<br>PANTHENOL<br>HYDROXYPROPYLTRIMONIUM HONEY<br>PEARL POWDER<br>*HELIANTHUS ANNUUS* (SUNFLOWER) SEED EXTRACT<br>*CITRUS MEDICA LIMONUM* (LEMON) PEEL EXTRACT<br>*CHAMOMILLA RECUTITA* (MATRICARIA) FLOWER EXTRACT<br>HONEY EXTRACT<br>*TRITICUM VULGARE* (WHEAT) GERM EXTRACT<br>*CAMELLIA SINENSIS* LEAF EXTRACT<br>*THEOBROMA CACAO* (COCOA) EXTRACT<br>LECITHIN<br>MAGNESIUM ASCORBYL PHOSPHATE<br>*FRAGARIA VESCA* (STRAWBERRY) FRUIT EXTRACT<br>*ZINGIBER OFFICINALE* (GINGER) ROOT EXTRACT<br>MICA<br>TITANIUM DIOXIDE<br>IRON OXIDES | The amounts and each of the one or more ingredients can be varied to achieve desired characteristics for the composition. |

The composition may contain one or more of the above listed solvents in an amount of 1 to 50 percent by weight based on the total weight of the composition. The composition may also contain one or more of the above listed non-aqueous components in an amount of 1 to 30 percent by weight based on the total weight of the composition. The acid dyes may be used either singly or in any combination thereof. They may be incorporated in an amount of 0.001-5% by weight, particularly 0.005-4% by weight, more particularly 0.2-3% by weight, based on the total weight of the composition. The composition may contain a buffer/acid system comprising one or more of citric acid, malic acid and sodium hydroxide to achieve a pH of 2 to 6 for the composition. The composition may also contain water and one or more of the other above listed excipient ingredients. The amounts of each of the one or more excipient ingredients can be varied to achieve desired characteristics for the composition.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A composition comprising:
   one or more acid direct dyes;
   an organic solvent; and
   an oil phase;
   wherein the oil phase content of the composition is from 2.0 to 3.0 percent by weight based on the total weight of the composition; wherein the composition has a pH of 2-6; and wherein the oil phase comprises cyclopentasiloxane and dimethiconol.

2. The composition of claim 1 in the form of a gel, a cream, a liquid or a foam.

3. The composition of claim 1 further comprising a component selected from the group consisting of: *Theobromo Cacao* Extract; *Camellia Sinensis* Leaf Extract; *Zingiber Officinale* Leaf Extract; *Punic Granatum* Leaf Extract; *Helianthus Annuus* (Sunflower) Seed Oil; and *Triticum Vulgare* (Wheat) Germ Extract.

4. The composition of claim 1, wherein the composition further comprises a carboxylic acid compound.

5. The composition of claim 4, wherein the carboxylic acid compound is selected from the group consisting of citric acid, malic acid and combinations thereof.

6. The composition of claim 1, wherein the organic solvent is propylene carbonate.

7. The composition of claim 1, further comprising ethanol.

8. The composition of claim 1, further comprising xanthan gum.

9. The composition of claim 1, further comprising sodium hydroxide.

10. The composition of claim 1, wherein the organic solvent is propylene carbonate, the composition further comprising:
    ethanol; and
    a carboxylic acid compound.

11. The composition of claim 1, wherein the composition is an oil-in-water dispersion.

12. A method comprising:
    applying the composition of claim 1 to hair;
    allowing the composition to remain on the hair; and
    subsequently rinsing the composition from the hair with water.

13. The method of claim 12, further comprising:
    washing the hair before applying the composition to the hair;
    wherein the hair is wet when the composition is applied thereto.

14. The method of claim 12, further comprising:
    applying conditioner to the hair and rinsing the conditioner from the hair after washing the hair and before applying the composition to the hair.

15. The method of claim 12, wherein the composition is left on the hair for at least three minutes prior to rinsing.

16. The method of claim 12, wherein the hair has been dyed with an oxidative hair dye composition prior to applying the composition to the hair.

* * * * *